US009668916B2

(12) United States Patent
Thompson

(10) Patent No.: US 9,668,916 B2
(45) Date of Patent: Jun. 6, 2017

(54) CONJUNCTIVAL COVER AND METHODS THEREFOR

(71) Applicant: Vance M. Thompson, Sioux Falls, SD (US)

(72) Inventor: Vance M. Thompson, Sioux Falls, SD (US)

(*) Notice: Subject to any disclaimer, the term of this patent is extended or adjusted under 35 U.S.C. 154(b) by 264 days.

(21) Appl. No.: 14/071,240

(22) Filed: Nov. 4, 2013

(65) Prior Publication Data

US 2015/0126970 A1 May 7, 2015

(51) Int. Cl.
*A61K 9/00* (2006.01)
*A61F 9/00* (2006.01)

(52) U.S. Cl.
CPC .......... *A61F 9/0017* (2013.01); *A61K 9/0051* (2013.01)

(58) Field of Classification Search
CPC .................................................. A61K 9/0051
See application file for complete search history.

(56) References Cited

U.S. PATENT DOCUMENTS

| 3,973,838 | A | 8/1976 | Page |
| 3,995,635 | A | 12/1976 | Higuchi et al. |
| 4,157,864 | A | 6/1979 | Koller et al. |
| 4,652,099 | A | 3/1987 | Lichtman |
| 8,506,944 | B2 | 8/2013 | Sullivan et al. |
| 2004/0096477 | A1 | 5/2004 | Chauhan et al. |
| 2010/0092452 | A1 | 4/2010 | Sullivan et al. |
| 2010/0233241 | A1 | 9/2010 | Leahy et al. |
| 2011/0059902 | A1 | 3/2011 | Sullivan et al. |
| 2011/0070222 | A1 | 3/2011 | Sullivan et al. |
| 2011/0142908 | A1 | 6/2011 | Sullivan et al. |
| 2011/0184358 | A1* | 7/2011 | Weiner ................. A61F 9/0017 604/290 |
| 2011/0282328 | A1 | 11/2011 | Ambati et al. |
| 2012/0245444 | A1 | 9/2012 | Otis et al. |
| 2012/0321611 | A1 | 12/2012 | Sullivan et al. |
| 2013/0261569 | A1 | 10/2013 | Weiner et al. |

FOREIGN PATENT DOCUMENTS

| EP | 2 276 496 | 1/2011 |
| EP | 2 276 497 | 1/2011 |
| EP | 2 632 532 | 9/2013 |
| WO | WO 01/33284 A1 | 5/2001 |
| WO | WO 2007/008666 A2 | 1/2007 |
| WO | WO 2009/137602 A1 | 11/2009 |

(Continued)

OTHER PUBLICATIONS

Ciolino et al., "In vivo performance of a drug-eluting contact lens to treat glaucoma for a month", Biomaterials, 35 (2014), 432-439.

(Continued)

*Primary Examiner* — Benjamin Packard
(74) *Attorney, Agent, or Firm* — Patterson, Thuente Pedersen, P.A.

(57) ABSTRACT

A conjunctival cover including an annular generally curved shell having a conjunctival portion structured to conform to and overly at least part of the conjunctiva of an eye. The annular generally partially spherical shell defines a generally central opening. The central opening is sized to leave a cornea of the eye substantially or partially uncovered when the conjunctival cover is applied to the eye.

16 Claims, 7 Drawing Sheets

(56) References Cited

FOREIGN PATENT DOCUMENTS

| WO | WO 2009/137603 A1 | 11/2009 |
| WO | WO 2010/105130 A2 | 9/2010 |
| WO | WO 2011/050287 A1 | 4/2011 |
| WO | WO 2012/058382 A2 | 5/2012 |

OTHER PUBLICATIONS

Severinsky et al., "Current applications and efficacy of sclera contact lenses—a retrospective study", 2010, 5 pages.
"Innovative drug-dispensing contact lens delivers glaucoma medication continuously for a month", Ophthalmology, Dec. 9, 2013, 2 pages.
PCT International Search Report for International Application No. PCT/US2014/063696, Feb. 12, 2015.
Written Opinion for International Application No. PCT/US2014/063696, Feb. 12, 2015.
International Preliminary Report on Patentability for International Application No. PCT/US2014/063696 dated May 10, 2016.
Written Opinion for International Application No. PCT/US2014/063696 dated Feb. 12, 2015.

* cited by examiner

CONJUNCTIVAL COVER AND METHODS THEREFOR

FIELD OF THE INVENTION

The invention relates generally to the field of treatment of dry eye syndrome and to the field of medication delivery by inserts.

BACKGROUND OF THE INVENTION

Contact lenses have been in existence for many decades. Early contact lenses were made of glass or rigid plastic such as polymethylmethacrylate. Early contact lens designs were quite large and referred to as scleral or haptic lens. Scleral or haptic contact lens designs cover the cornea completely as well as covering a large portion of the conjunctiva or sclera of the eye. The sclera is the structural white of the eyeball while the conjunctiva is a transparent tissue which overlies the sclera as well as covering the backside of the eye lids. Early contact lens designs were made of rigid, largely oxygen impermeable polymers as discussed above or a very few of glass. Because cornea philosophy was poorly understood at the time these lenses were made, they often cause great discomfort and negative effect on the corneal health.

As time went by, in the 1950's, hard contact lenses made of polymethylmethacrylate became much smaller having a diameter significantly smaller than that of the cornea. Hard corneal contact lenses were more comfortable and less physiological damaging than scleral or haptic lenses, but only marginally so. Hard contact lenses still significantly deprived the cornea of a necessary oxygen supply from atmospheric oxygen to maintain good corneal health and were difficult to adapt to. In the 1970s, so called soft corneal contact lenses became available. Soft contact lenses generally were larger than hard corneal contact lenses having a diameter approximating that of the cornea, somewhat larger than the cornea or somewhat smaller than the cornea. Soft contact lenses are generally made of hydrophilic polymers that absorb substantial amounts of water, saline solution or the tear film. Soft contact lenses also provided improved comfort due to their permeability to oxygen and due to their more flexible nature. Later still, so called gas-permeable contact lenses became available. Gas permeable rigid contact lenses are similar in size and structure to hard corneal contact lenses but are made of rigid oxygen permeable polymers that allow oxygen and other gases to pass through the material of the contact lens to provide improved corneal health. Generally, rigid contact lenses provide sharper vision than soft contact lenses though this is not universally true.

Hard contact lenses are well as scleral or haptic contact lenses were sometimes fenestrated. That is, tiny holes were drilled or otherwise formed through the rigid contact lens material in an effort to improve tear exchange under the contact lens or to provide a greater availability of oxygen through the contact lens. Fenestration was generally not a very successful technique. Fenestrations, however, were uniformly tiny holes generally much smaller than one millimeter in diameter, occasionally multiple fenestrations were present.

All contact lenses known to the applicants provide substantially or complete coverage of the cornea of the eye.

Drug delivery inserts are also known to exist. Drug delivery inserts are small containers into which drugs or pharmaceuticals are placed or absorbed that exist in several different forms. Subpalpebral drug delivery inserts are generally intended to be inserted behind the eye lid in the conjunctival fornices and to gradually release a desired medication to provide a slow, continuous supply of drug to the eye. Subpalpebral drug delivery inserts generally have suffered from being uncomfortable for the patient to tolerate and subject to be accidentally dislodged from the eye by rubbing of the eye or other movements. In addition, subpapebral drug delivery inserts sometimes cause irritation of the conjunctiva or the eye lids.

Another variety of drug delivery insert is intended to be surgically inserted within the globe of the eye to gradually leach out a steady supply of a desired drug into the intraocular environment. Intraocular drug delivery inserts are less often used due to their relatively invasive nature.

Generally, drug delivery inserts whether subpalpebral or intraocular have contained a single drug.

Dry eye syndrome is one of the most commonly treated eye problems in the United States. Dry eye syndrome is also known as keratitis sicca, keratoconjunctivitis sicca (KCS) xerophthalmia, and lacrimal insufficiency. It is estimated that over ten million Americans and 30 million persons worldwide suffer from dry eye syndrome.

For a large fraction of dry eye patients, dry eye syndrome creates discomfort or annoyance. For those severely afflicted, dry eye syndrome can be debilitating and, in some circumstances, even sight-threatening. In extremely severe cases, dry eye syndrome can even lead to the loss of an eye.

Dry eye syndrome typically results from deficiency in the quality or quantity of tears produced by the patient. Precorneal tear film has traditionally been considered to have a three-layered structure. The closest to the cornea lies the mucin, or mucus, layer. The mucin layer provides an interface between the corneal epithelium and the remainder of the tear film. Overlying the mucin layer is the watery aqueous layer, which is the thickest layer of the three. The outermost layer of the precorneal tear film is the lipid layer. The lipid layer is an oily film that reduces evaporation from the aqueous layer beneath it.

The middle aqueous layer provides moisture to the corneal tissue, carries important nutrients, and serves to remove metabolic waste produced by the cornea. Deficiency in any of the three layers of the precorneal tear film can result in complaints of dry, gritty feeling or burning eyes.

The mucin that forms the mucin layer, nearest the cornea, is secreted by goblet cells in the conjunctiva. The conjunctiva is the transparent tissue that covers the sclera and the backside of the eyelids. The mucin layer functions to decrease surface tension of the tear film. In addition, the cornea itself is hydrophobic. Without the mucin layer to provide a bridge between the cornea and the aqueous layer, the aqueous layer would bead up and allow dry spot formation on the cornea.

The aqueous layer is secreted primarily by the glands of Wolfring and Krause located in the eyelid margin. The aqueous layer helps provide an optically smooth, transparent surface to the precorneal tear film. The lipid layer is secreted by the meibomian glands, and the glands of Zeiss and Moll. The glands of Zeiss and Moll are also located at the eyelid margin.

Blinking is essential to maintenance of the precorneal tear film. During each blink, the eyelid wipes over the surface of the cornea, smoothing the mucin layer and spreading the overlying aqueous and lipid layers to provide a completely wetted surface. In between blinks, the tear film thins due to evaporation of the aqueous layer. If evaporation is excessive, dry spots may form on the surface of the cornea.

Deficiency, or imperfect quality, of any of the three component layers can lead to dry eye symptoms. Many systemic and external factors can contribute to dry eye syndrome. For example, Sjogren's syndrome is associated with arthritic diseases in combination with dry eye and dry mouth. Deficiency of Vitamin A, use of oral contraceptives and environmental factors can all contribute to dry eye syndrome.

Recent research into the natural history of dry eye syndrome has shown that the disease progresses through four stages. Each stage is a consequence of the preceding stage. The stages are:

1. Loss of water from the aqueous layer of the tear film leading to an increase in the tear film osmolarity;
2. Loss of conjunctival goblet cells and decreased corneal glycogen;
3. Increased loss of corneal squamous epithelial cells;
4. Destabilization of the interface between the corneal surface and the tear film.

Either decreased secretion of tear film components or increased evaporation lead to increased tear film osmolarity and the following stages that lead to eventual corneal decompensation and the serious consequences of dry eye syndrome.

The adnexa of the eye may also be involved in dry eye syndrome. The adnexa of the eye include the structures surrounding the eye such as the eyelids, eye lashes, the tear drainage and tear production structures. Blepharitis commonly contributes to dry eye syndrome. Blepharitis typically results from bacterial infection of the tiny glands in the margin of the eyelid. These glands include the glands of Zeiss, Moll and Wolfring as well as the meibomian glands. Most commonly, the affected glands are the meibomian glands. In bacterial blepharitis, bacterial infection causes the meibomian glands to become plugged, and thus not be able to produce a normal lipid layer to contribute to the tear film. Some bacteria that infect the glands also secrete exotoxins that seep out of the glands into the eye and injure the corneal epithelium.

Treatments of dry eye syndrome vary depending upon the type of presentation. The most common treatment for dry eye syndrome is the use of artificial tear supplements to provide additional moisture and lubrication to the corneal surface. Artificial tear eye drops are placed on the eye by the patient. Artificial tear supplements must be used regularly and often to be effective.

Lubricant ointments may also be employed. Ointments are usually used at bedtime because they tend to be messy and blur vision. For some patients, even the use of ointments is not sufficient to provide comfort during sleep.

Tears drain from the eye through the lacrimal drainage system. Tiny openings at the nasal corner of each upper and lower eyelid are called the lacrimal puncta. The lacrimal puncta lead into ducts that drain into the nasopharynx.

One treatment for dry eye syndrome is to partially or completely close one or more lacrimal puncta to reduce tear outflow into the lacrimal drainage apparatus. Traditionally, this closure was accomplished surgically or by cautery. In the last decade, however, temporary and permanent punctal occlusion plugs have been utilized.

Permanent punctal plugs are typically made from surgical silicone; temporary plugs are generally made of soluble collagen. Collagen plugs dissolve over a period of days and are helpful in diagnosis.

Punctal plugs are placed into the lacrimal puncta, or lacrimal drainage ducts. The plugs impede the outflow of tears from the eye. This approach slows the outflow of tears and retains them in the eyes longer, often relieving symptoms. Punctal plugs have the distinct advantage of being readily removable and avoid the issues of scar formation.

Blepharitis is sometimes treated by the use of antibiotic medications. Another important treatment for blepharitis is the application of warm soaks and lid scrubs. In this form of treatment, the patient applies a warm wet washcloth to the eyelids for a period of time to provide humidity, warmth and to help soften blockage of and restore flow from the meibomian glands. Lid scrubs are practiced by taking a mild, nonirritating soap and vigorously scrubbing the eyelid margins with they eyes closed, so as to massage the meibomian glands and increase production. The surfactant helps to dissolve the greasy blockage of the meibomian glands.

Patients who have severe dry eye syndrome often suffer disrupted sleep because they cannot go for longer than an hour or so without applying tear supplements to the eyes. This can lead to pronounced sleep deprivation and a consequent reduction in quality of life.

A variety of researchers have been seeking other medicinal treatments for dry eye syndrome. Largely, this research is directed at pharmaceutical efforts to increase tear production.

Despite the many treatment options available, there remains no cure for dry eye syndrome. A great many patients still have substantial and even debilitating discomfort because of dry eye syndrome. Very few treatment options exist to provide comfort for dry eye syndrome patients during sleep.

Accordingly, there is still room for improvement in the arts of treating dry eye syndrome and in the art of drug delivery inserts.

SUMMARY OF THE INVENTION

According to one embodiment of the invention, many of the above discussed problems are solved by an annular conjunctival cover. In the context of the invention, annular does not necessarily limit the invention to a circular structure with an opening in the center. The invention is annular in the sense that it covers the conjunctiva surrounding the cornea while leaving the cornea completely or substantially uncovered. The conjunctival cover make take other shapes as described and depicted herein while still being "annular" in the sense of the invention. According to one embodiment of the invention, the cornea is left completely uncovered and exposed. According to another embodiment of the invention, at least 80% of the corneal diameter is left uncovered and exposed. According to another embodiment of the invention, at least 50% of the corneal diameter is left uncovered and exposed.

Accordingly, the annular conjunctival cover generally covers the conjunctiva partially or completely but does not the cornea completely. According to an embodiment of the invention, the cornea is not covered by the annular conjunctival shield centrally. The cornea may have some coverage in the peripheral portions.

According to one embodiment of the invention, the conjunctival cover retains mucin and aqueous tear components under the cover. In this embodiment, the conjunctival cover provides a reservoir of tears so that with blinking the reservoir of tears, or mucin and aqueous tear components is flushed out from under the conjunctival cover and is directed to the cornea to assist in promoting corneal health.

According to another embodiment of the invention, evaporation of tears from the conjunctival surface is reduced.

According to another embodiment of the invention, the cornea is partially covered to allow shaping of the anterior corneal tear film over the central cornea in such a way as to be corrective for vision. According to this embodiment of the invention, a tear film lens would be created though not in the sense of a tear lens that is created between a rigid contact lens and the cornea but in the sense that an alteration of the curvature of the tear film overlying the central uncovered cornea is altered to provide some vision correction. The conjunctival cover may or may not have optical power of its own but structure surrounding the central opening may be varied to create a tear lens in the central opening that may contribute to correction of myopia, hyperopia, astigmatism or presbyopia. The tear lens of the central opening may also provide a prismatic correction based on structure surrounding the central opening.

According to one embodiment of the invention, the curvature of the annular conjunctival cover is flatter than that of the conjunctival surface. According to another embodiment of the invention, the curvature of the annular conjunctival cover approximately parallels the conjunctival surface. According to yet another embodiment of the invention, the annular conjunctival cover is steeper in curvature than the covered conjunctival surface.

According to another embodiment of the invention, the annular conjunctival cover has an overall diameter approximating that of the palpebral fissure so that an outer edge of the annular conjunctival cover extends substantially into the fornices superiorly and inferiorly. According to another embodiment of the invention, the annular conjunctival cover has a diameter significantly less than the diameter required to extend to the fornices. According to another embodiment of the invention, the annular conjunctival cover is not circular but instead has a spindle or football shaped so as to cover the otherwise exposed nasal and lateral conjunctiva more completely than the superior and inferior conjunctiva. In this case, the annular conjunctival cover may optionally include a prism ballast wherein the lower portion of the annular conjunctival cover is thicker than the upper portion or other ballast to encourage desired positioning.

The annular conjunctival cover, according to another example embodiment of the invention, is formed from materials similar to those used to make soft contact lenses. For example, the annular conjunctival cover may be formed of collagen, hydrophilic polymers or non-hydrophilic polymers of a flexible nature. The annular conjuctival cover may be formed in a single layer or may include multiple layers.

The annular conjuctival cover according to another example embodiment of the invention may include a drug delivery function. For example, the annular conjunctival cover may include one or more physical reservoirs into which a drug desired to be delivered to the eye is placed. According to another example embodiment, a drug to be administered in an aqueous solution or suspension may be absorbed into hydrophilic material of the annular conjunctival cover. Other non aqueous or partially aqueous vehicles may also be used. According to yet another embodiment of the invention, multiple drug reservoirs may be present so that multiple drugs may be delivered to the eye simultaneously from different individual reservoirs without the mixing of the drugs into a single delivery medium.

When the annular conjunctival shield is utilized as a drug delivery mechanism, drugs delivered may include antibiotics, steroids, anti-glaucoma medications, anti-viral medications, anti-viral medications, NSAIDS, ocular surface lubricants and other drugs useful in treating dry eye including cyclosporine to inhibit the inflammatory response.

Further drugs or active agents that can be delivered by drug delivery conjunctival cover include, for example, but are not limited to: Anti-infectives: such as antibiotics, including tetracycline, chlortetracycline, bacitracin, neomycin, polymyxin B, gramicidin, oxytetracycline, chloramphenicol, and erythromycin; sulfonamides, including sulfacetamide, sulfamethizole, sulfisoxazole; quinolones, including ofloxacin, norfloxacin, ciprofloxacin, sporfloxacin; aminoglycosides, including amikacin, tobramycin, gentamicin; cephalosporins; combinations of antibiotics; antivirals, including idoxuridine, trifluridine, vidarabine cidofovir, foscarnet sodium, ganciclovir sodium and acyclovir; antifungals such as amphotericin B, nystatin, flucytosine, fluconazole, natamycin, miconazole and ketoconazole; and other anti-infectives including nitrofurazone and sodium propionate.

Anti-allergy medications such as antzoline, methapyriline, chlorpheniramine, pyrilamine and prophenpyridamine, emedastine, ketorolac, levocabastin, lodoxamide, loteprednol, naphazoline/antazoline, naphazoline/pheniramine, olopatadine and cromolyn sodium. Anti-inflammatories: such as hydrocortisone, hydrocortisone acetate, dexamethasone, dexamethasone 21-phosphate, fluocinolone, medrysone, prednisolone, prednisolone 21-phosphate, prednisolone acetate, fluorometholone, fluorometholone acetate, meddrysone, loteprednol etabonate, rimexolone. Nonsteroidal anti-inflammatories: such as flurbiprofen, suprofen, diclofenac, indomethacin, ketoprofen, and ketorolac. Decongestants: such as phenylephrine, naphazoline, oxymetazoline, and tetrahydrazoline. Miotics and anticholinesterases: such as pilocarpine, eserine talicylate, carbachol, diisopropyl fluorophosphate, phospholine iodide, and demecarium bromide.

Mydriatics: such as atropine sulfate, cyclopentolate; homatropine, scopolamine, tropicamide, eucatropine, and hydroxyamphetamine.

Other medications include but are not limited to antiglaucoma agents: such as adrenergics, including epinephrine and dipivefrin, epinephryl borate; .beta.-adrenergic blocking agents, including levobunolol, betaxolol, metipranolol, timolol, carteolol; alpha.-adrenergic agonists, including apraclonidine, clonidine, brimonidine; parasympathomimetics, including pilocarpine, carbachol; cholinesterase inhibitors, including isoflurophate, demecarium bromide, echothiephate iodide; carbonic anhydrase inhibitors, including dichlorphenamide acetazolamide, methazolamide, dorzolamide, brinzolamide, dichlorphenamide; prostaglandins, including latanoprost, travatan, bimatoprost; diconosoids and combinations of the above, such as a .beta.-adrenergic blocking agent with a carbonic anhydrase inhibitor.

Anticataract drugs: such as aldose reductase inhibitors including tolerestat, statol, sorbinil; antioxidants, including ascorbic acid, vitamin E; nutritional supplements, including glutathione and zinc.

Lubricants: such as glycerin, propylene glycol, polyethylene glycol and polyglycerins may also be delivered. Omega 3 fatty acids and vitamin supplements may also be delivered. The annular conjunctival cover may be used to deliver any drug that would otherwise be delivered in an eye drop or ointment or by injection or other routes of administration.

The annular conjunctival cover can release drugs through diffusion out of it if the drug is absorbed therein or by gradual dissolving of the walls of the drug reservoirs. Drugs can be released at different time periods by structuring the drug reservoirs for differential times of dissolution such as by variable wall thickness. Drugs may also be released through active pumping from blinking or through stronger active pumping through active eye squeezing by the patient.

In addition, the annular conjunctival cover may be made of materials that are bioabsorbable or non-absorbable. Similar to contact lenses, the annular conjunctival cover may be designed for short term or extended use. For example, the device may be designed for single day use, weekly use, monthly use, six month use, one year use or longer.

According to another embodiment of the invention, the annular conjunctival cover may be intrapalpebral in nature in that it covers the conjunctiva where it is normally exposed with the eye open between the eyelid margins. According to another embodiment of the invention, mucous and aqueous components of the tear film that form the natural lubricants of the eye are present on the conjunctiva and thus susceptible to evaporation into the environment. For an individual with normal adequate tear production this is generally not a problem. For a dry eye patient controlling tear evaporation may make a large difference in comfort and ocular anterior segment health. According to one embodiment of the invention, the tear film may be contained or preserved between the annular conjunctival cover as well as being present overlying the annular conjunctival cover. Thus, the tear film would be divided into two residence locations, one between the device and the conjunctiva and another on top of the annular conjunctival cover. This dual reservoir of tear film is expected to be directed onto the cornea at the time of a blink, the overlying tear film by the normal blinking mechanism and the underlying tear film by the squeezing or pressing of the annular conjunctival cover against the conjunctiva by the action of the eyelids. Further tear reservoirs can be provided by forming the conjunctival cover to have multiple layers that may define multiple tear reservoirs. Normal or intentional eye movements are expected to also contribute to distribution of tears from two or more tear reservoirs to the corneal surface. For example, if a blink does not expel a majority of tear contents held under the lower lid the patient might learn to look upward and the straight ahead to such that the lower eyelid margin presses or squeezes the tears onto the cornea in the manner of a squeegee. The same may be found true for medications in drug reservoirs. A blink may express a certain amount but purposeful upward or downward gaze may be found to squeeze out further tears or medication onto the corneal surface. Forcefully closing the eyes may be another way to expel contents that reside in or under the conjunctival cover or in the drug reservoirs because of the squeezing effect of the eye lids against the globe. Patients may be directed to do so to expel more contents on demand. Digital massage over the upper or lower eyelid may be utilized to expel tear contents or the contents of drug reservoirs.

The conjunctival cover may also be used for sampling purposes. The conjunctival cover may be placed on the eye to absorb tears or other desired substances that may then be recovered for laboratory testing for, for example, but not limited to diagnostic testing for dry eye tests, sugar content, or other tests.

According to one example embodiment of the invention, the annular conjunctival cover is a single use disposable product. According to another embodiment of the invention, the annular conjunctival cover is structured for multiple uses with associated cleaning and disinfection as needed and desired.

According to another embodiment of the invention, the conjunctival cover may incorporate an intraocular pressure monitor or other monitor that monitors one or more ocular functions. For example, the conjunctival cover may incorporate a strain gauge or intraocular pressure monitor similar to that of the Sensimed Triggerfish by Sensimed of Switzerland.

According to another example embodiment of the invention, the conjunctival cover may incorporate transparent or opaque tinting or portions. This can be utilized to, for example, obscure unsightly scars or pigmentation of the conjunctiva as well as for cosmetic purposes. Tinting may be used to change the color of the conjunctiva for fun or may include an onlay, inlay or temporary tattoo.

According to another embodiment of the invention, the invention includes a method in which a physician or other health professional places the annular conjunctival cover on the eye where it remains until being removed by the physician. Alternately, a patient may place and remove the annular conjunctival cover on the eye thus providing an opportunity to rehydrate or reload the annular conjunctival cover with a lubricant or a drug medication to be delivered, thus, relieving the patient of the necessity to use eye drops several times during the day or for whatever other period of time that drops are generally used or, at least reducing the frequency at which eye drop application is required. This also provides for a continuous supply of medication being delivered on a continuous basis.

According to another example embodiment, medication is housed within the annular conjunctival cover in multiple individual reservoirs that are formed of an absorbable materials that degrades over time.

DETAILED DESCRIPTION OF THE DRAWINGS

Figure 1:
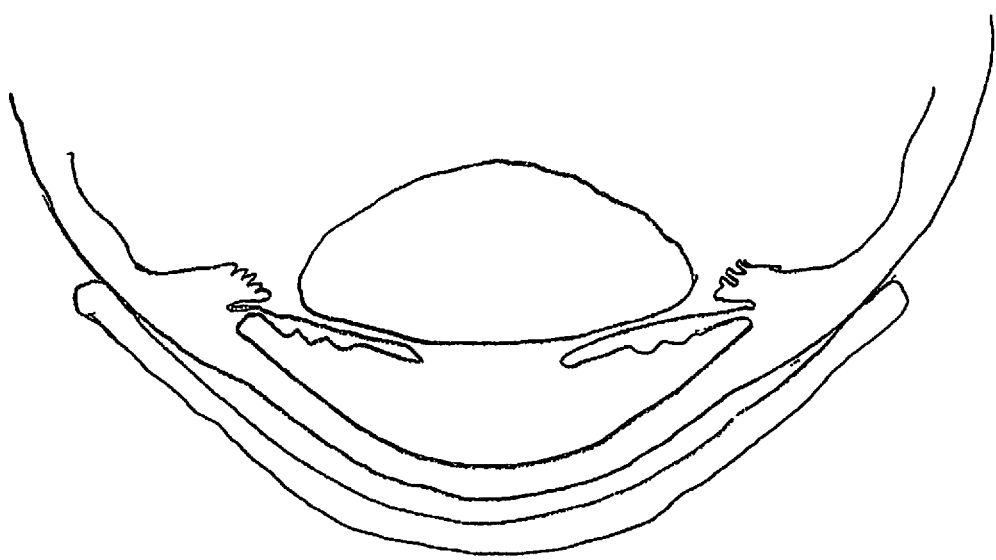
FIG. 1 is a schematic depiction of a prior art scleral contact lens.
Figure 2:
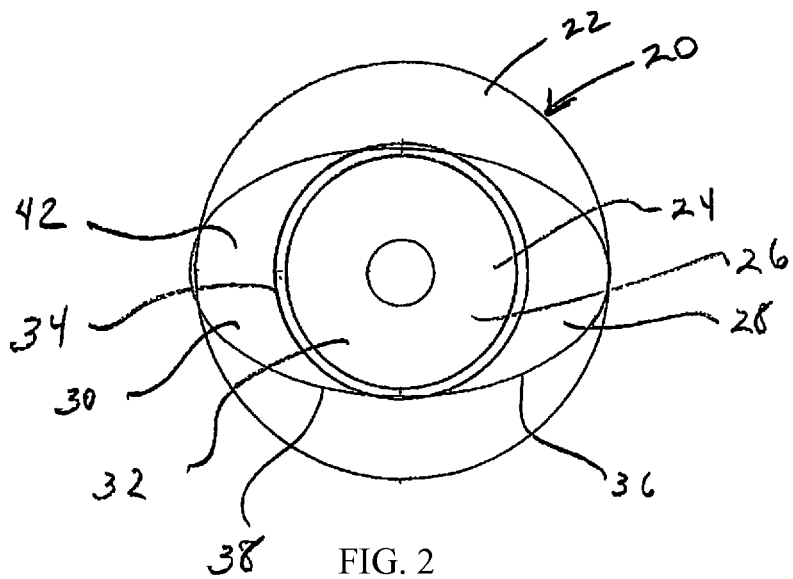
FIG. 2 is a schematic depiction of an annular conjunctival cover applied to an eye according to an example embodiment of the invention.

Referring generally to FIG. 1-10, conjunctival cover 20 according to an embodiment of the invention, generally includes annular shell 22 presenting central opening 24. Annular shell 22 is formed of a hydrophilic or non-hydrophilic flexible material similar to those used in the manufacture and construction of soft contact lenses. Conjunctival cover 20 is utilized in relation to an eye 26. Eye 26 generally includes sclera 28, conjunctiva 30, cornea 32, limbus 34 and eyelids 36. The sclera is the structural white portion of the eye that forms the majority of the eyeball. Conjunctiva 30 overlies the sclera and includes palpebral conjunctiva 40 and bulbar conjunctiva 42. Palpebral conjuctiva 40 and bulbar conjuctiva 42 meet at fornices 44. Cornea 32 is the clear front part of the eye and is generally dome shaped in structure. Limbus 34 is the juncture between the edge of the cornea 32 and sclera 28. Conjunctival cover 20 generally covers bulbar conjuctiva 42 while leaving all or a portion of cornea 32 exposed. For this purpose, central opening 24 is positioned to generally coincide with cornea 32. Annular shell 22 of conjunctival cover 20 may be sized to extend into fornices 44 or may be smaller in size.

Figure 3:
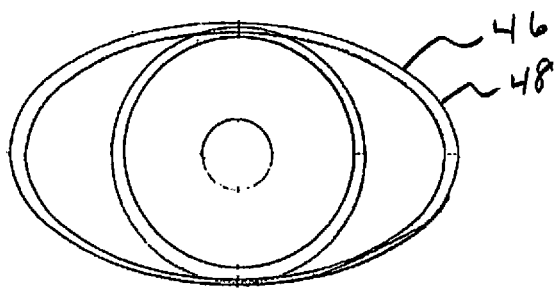
FIG. 3 is a is a schematic depiction of an elliptical annular conjunctival cover applied to an eye according to an example embodiment of the invention.
Figure 4:
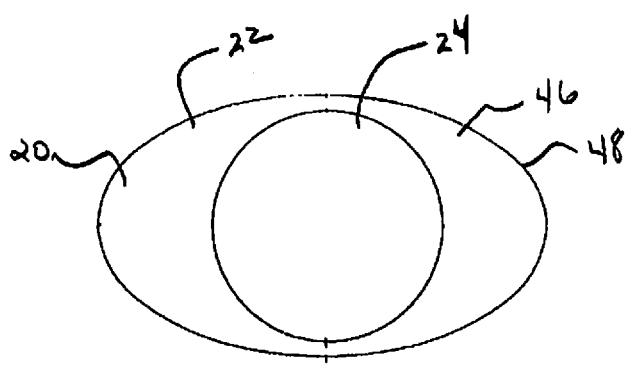
FIG. 4 is a schematic depiction of an elliptical annular conjunctival cover isolated from the eye according to an example embodiment of the invention.

Referring to FIGS. 3 and 4, another embodiment of conjunctival cover 20 is elliptical conjunctival cover 46. Elliptical conjunctival cover 46 includes annular shell 22 having generally elliptical peripheral margin 48. Elliptical conjunctival cover 46 may be sized so that elliptical peripheral margin 48 is generally coincident with eyelid margins 38. Accordingly, elliptical peripheral margin 48 may extend partially under eyelid margins 38 or may be slightly smaller than the space bounded by eyelid margins 38 when eye 26 is open.

Figure 5:
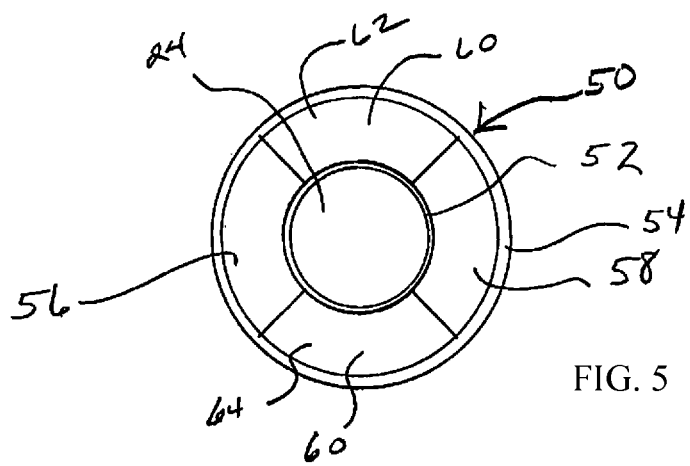
FIG. 5 is a schematic depiction of a conjunctival cover having an inner ring, an outer ring and a segmented structure according to an example embodiment of the invention.
Figure 6:
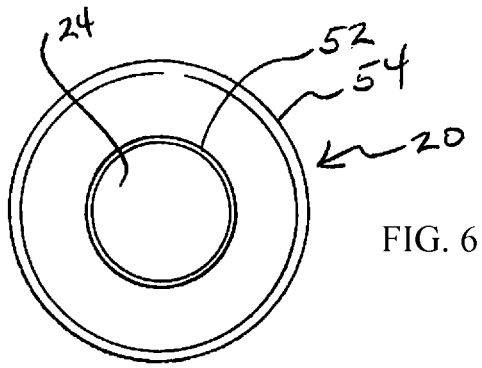
FIG. 6 is a schematic depiction of an annular conjunctival cover according to an example embodiment of the invention.

Referring now to FIG. 5, another embodiment of conjunctival cover 20 is depicted. Dual ring conjunctival cover 50 generally includes inner ring 52, outer ring 54, nasal cover portion 56 and temporal cover portion 58 Inner ring 52 approximates the corneal diameter being slightly larger or slightly smaller than the limbus. Outer ring 54 is larger than inner ring 52 and may be sized to extend partially or completely into fornices 44 Inner ring 52, outer ring 54, nasal cover portion 56 and temporal cover portion 58 together define arcuate openings 60. Arcuate openings 60 include superior arcuate opening 62 and inferior arcuate opening 64 Inner ring 52, outer ring 54, nasal cover portion 56 and temporal cover portion 58 may be integrally formed, for example, by a molding process or may be overmolded or otherwise assembled of separate structures.

Figure 7:
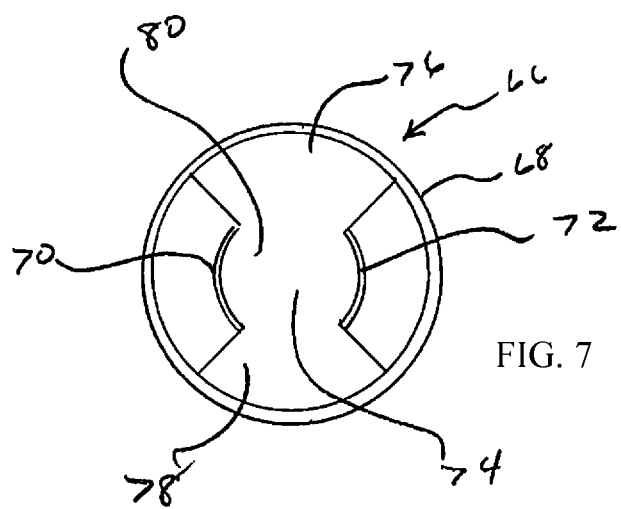
FIG. 7 is a schematic depiction of a conjunctival cover having a partial inner ring, an outer ring and a segmented structure according to an example embodiment of the invention.

Referring now to FIG. 7, another embodiment of conjunctival cover 20 is depicted. Partial inner ring conjunctival cover 66 generally includes outer ring 68, nasal inner ring segment 70, temporal inner ring segment 72, nasal cover portion 56 and temporal cover portion 58. These structure together define central opening 74 which includes superior opening portion 76, inferior opening portion 78 and central opening portion 80. Accordingly, when placed upon the eye, partial inner ring conjunctival cover 66 generally covers the nasal and temporal conjunctiva while not covering the superior and inferior conjunctiva which are covered by eyelids 36.

Conjunctival cover 20 may also include other fenestrations beyond those identified herein.

Figure 8:
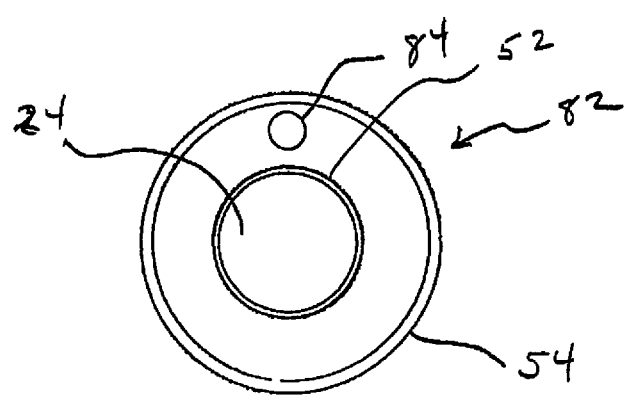
FIG. 8 is a schematic depiction of a conjunctival cover having a drug reservoir to support drug delivery capability according to an example embodiment of the invention.

Referring now to FIG. 8, another embodiment of conjunctival cover 20 is depicted. Drug delivery conjunctival cover 82 can be similar in structure to any of the above described conjunctival covers 20 but is adapted for drug delivery.

According to an embodiment depicted in FIG. 8, drug delivery conjunctival cover 82 includes first drug reservoir 84, second drug reservoir 86 and third drug reservoir 88. Drug delivery conjunctival cover 82 may include one or more drug reservoirs 90. Drug reservoirs 90 may be formed as cavities within drug delivery conjunctival cover 82 which are bounded by a material that is bio-absorbable or biodegradable in the eye environment. A wall thickness of first drug reservoir 84, second drug reservoir 86 and third drug reservoir 88 may vary in order to facilitate timed release of drug dosages. The first drug reservoir may have a thinner wall that is breached by bio-absorption or biodegradation sooner than the thicker walls of second drug reservoir 86 or third drug reservoir 88.

Drug delivery conjunctival cover 82 may also be formed of a hydrophilic material that absorbs an aqueous solution of a drug to be released for later diffusion into the ocular conjunctival environment. Thus, drug delivery conjunctival cover 82 may be formed of a poly-HEMA or another hydrophilic material known to those skilled in the contact lens arts.

Figure 9:
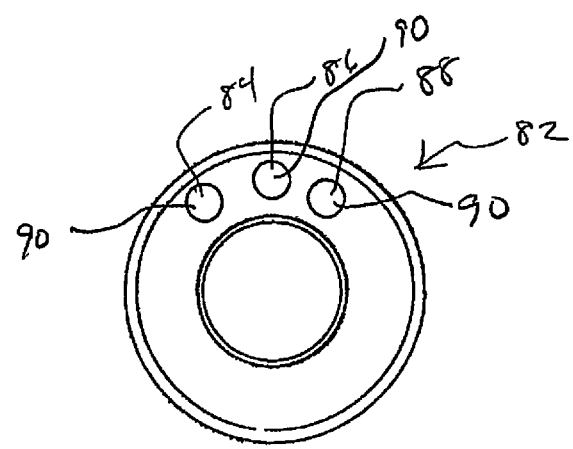
FIG. 9 is a schematic depiction of a conjunctival cover having multiple drug reservoirs to support drug delivery capability according to an example embodiment of the invention.
Figure 10:
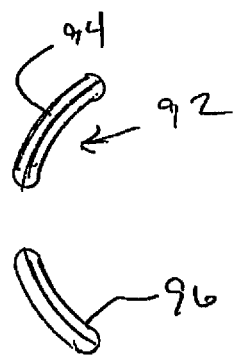
FIG. 10 is a schematic depiction of a conjunctival cover having multiple layers according to an example embodiment of the invention.
Figure 11:
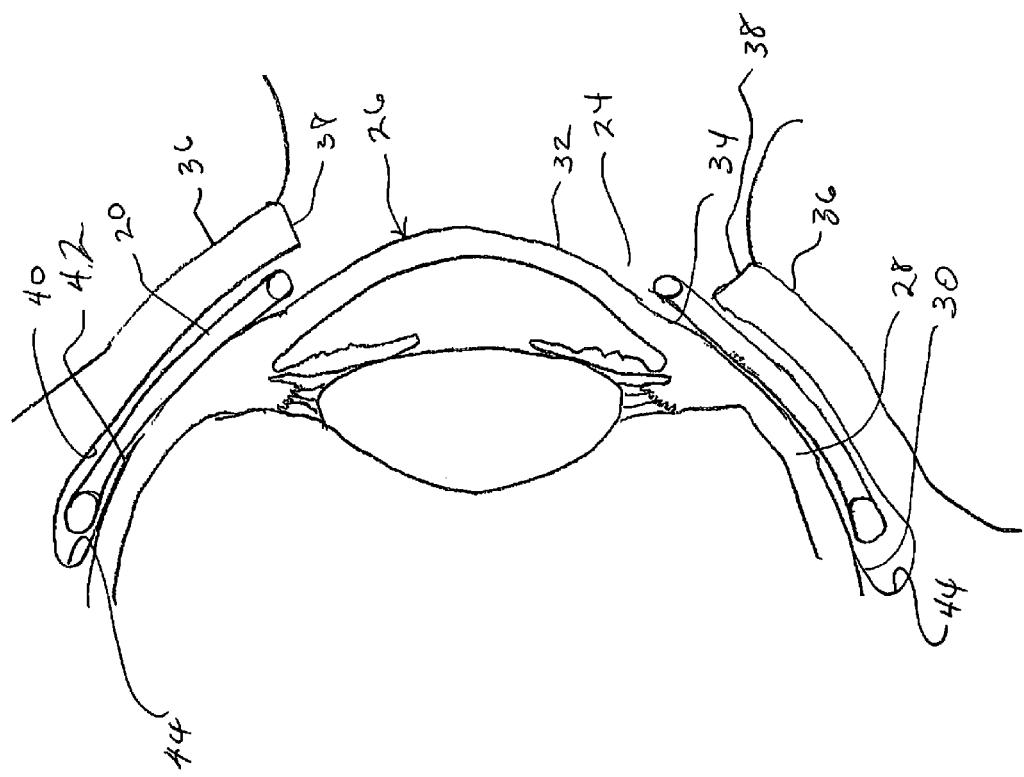
FIG. 11 is a schematic cross sectional view of a conjunctival cover applied to an eye according to an example embodiment of the invention.

Referring now to FIG. 9, another embodiment of conjunctival cover 20 is depicted in cross-section. Multi-layer conjunctival cover 92 includes at least first layer 94 and second layer 96. Multi-layer conjunctival cover 92 may have two or more layers of similar or different construction materials.

Drugs to be delivered by drug delivery conjunctival cover 82 may include but are not limited to antibiotics, steroids, glaucoma medications, antiviral medications, antifungal medications, NSAIDs, surface lubricants and anti-inflammatories such as cyclosporine.

Drug delivery conjunctival cover 82 may also be utilized to deliver nano-technology substances into the eye.

According to another example embodiment the invention includes a method of treating an eye, including applying an annular conjunctival cover to the eye by retracting the eyelids and placing the annular conjunctival cover on a bulbar conjunctiva of the eye while leaving a cornea of the eye substantially uncovered; and releasing the eye lids.

The method may further include incorporating a drug into the annular conjunctival cover prior to application.

The method may further include incorporating the drug into the annular conjunctival cover by exposing the annular conjunctival cover to the drug in solution or suspension such that the drug is absorbed into the annular conjunctival cover.

The method may further include incorporating the drug into the annular conjunctival cover by inserting the drug into a drug reservoir incorporated in the annular conjunctival cover.

The method may further include inserting multiple drugs into multiple separate drug reservoirs incorporated in the annular conjunctival cover.

In operation, various embodiments of conjunctival cover 20 are applied to conjunctiva 30 in a similar fashion to the application of a soft contact lens or a sclera contact lens. Various embodiments of conjunctival cover 20 may be applied to eye 26 by the patient or by a health care professional. Eyelids 36 are pulled open by using the fingers near the eyelids margins 38 and conjunctival cover 20 is placed upon the eye at least partially covering the conjunctiva 30. As discussed above, various embodiments of conjunctival cover 20 may partially or completely cover the conjunctiva 30 while partially or completely exposing the cornea 32. Various embodiments of conjunctival cover 20 trap mucin and other tear film components between conjunctival cover 20 and conjunctiva 30. The tear film also covers the external surface of conjunctival cover 20. Upon blinking, eyelids 36 and in particular eyelid margins 38 pass over conjunctival cover 20 and both wipes tear film components on the surface of conjunctival cover 20 onto cornea 32 and also squeezes or massages tear film components between conjunctival cover 20 and conjunctiva 30 onto cornea 32.

Elliptical conjunctival cover 46 covers conjunctiva 30 substantially between eyelid margins 38. Dual ring conjunctival cover 50 is placed on eye 26 so that nasal cover portion 56 covers nasal palpebral conjunctiva 40 while temporal cover portion 58 covers the temporal bulbar conjunctiva 42.

Partial inner ring conjunctival cover 66 is placed on eye 26 so that nasal cover portion 56 covers nasal bulbar conjunctiva 40 while temporal cover portion 58 covers temporal bulbar conjunctiva 42.

Drug delivery conjunctival cover 82 is placed on eye 26 where drugs absorb into drug delivery conjunctival cover 82 diffuse out into eye 26 and surrounding structures.

In the case of drug delivery conjunctival cover 82 having first drug reservoir 84 and optionally second drug reservoir 86 and third drug reservoir 88, drug reservoirs 90 dissolve at planned rate to provide time release of contained drugs into the eye.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

The invention claimed is:

1. A conjunctival cover comprising:
an annular generally curved shell having a conjunctival portion structured to conform to and overly at least part of a conjunctiva of an eye;
the annular generally partially spherical shell defining a generally central opening therethrough, the central opening being sized to leave a cornea of the eye substantially or partially uncovered when the conjunctival cover is applied to the eye; and
an inner ring portion and an outer ring portion, the inner ring portion bordering an inner edge of the conjunctival portion and the outer ring bordering an outer edge of the conjunctival portion and the conjunctival portion being divided into a nasal cover portion and a temporal cover portion, the nasal portion and the temporal portion being separated from each other by at least one of a superior opening portion and an inferior opening portion located at least one of superiorly and inferiorly.

2. The conjunctival cover as claimed in claim 1, wherein the inner ring portion forms a complete generally circular structure.

3. The conjunctival cover as claimed in claim 1, wherein the inner ring portion is segmented and comprises at least one generally arcuate portion.

4. The conjunctival cover as claimed in claim 1, wherein the conjunctival cover is formed from a flexible, biocompatible and ocularly compatible material.

5. The conjunctival cover as claimed in claim 1, wherein the conjunctival cover is sized so that outer edges thereof extend substantially to the conjunctival fornices.

6. The conjunctival cover as claimed in claim 1, wherein the conjunctival cover has a generally elliptical outer perimeter that is sized to conform approximately to the portion of the eye exposed between lid margins of eyelids.

7. The conjunctival cover as claimed in claim 1, wherein the conjunctival cover is formed at least partially from an absorptive material and further comprising a drug absorbed into the absorptive material for delivery.

8. The conjunctival cover as claimed in claim 1, further comprising a bioabsorbable or biodegradable material wherein the bioabsorbable or biodegradable material defines at least one drug reservoir.

9. The conjunctival cover as claimed in claim 8, wherein the at least one drug reservoir includes a first drug reservoir and a second drug reservoir, the first drug reservoir being structured to release a first contained drug aliquot after a first time period and the second drug reservoir being structured to release a second contained drug aliquot after a second time period that is different from the first time period.

10. The conjunctival cover as claimed in claim 1, further comprising at least a first layer and a second layer.

11. The conjunctival cover as claimed in claim 1, wherein the central opening is sized to leave more than fifty percent of the cornea uncovered.

12. A method of treating an eye, comprising:
applying an annular conjunctival cover to the eye by retracting the eyelids and placing the annular conjunctival cover on a bulbar conjunctiva of the eye while leaving a cornea of the eye substantially uncovered;
placing an inner ring portion of the conjunctival cover proximate the cornea and an outer ring portion proximate a conjunctival cul de sac,
placing a divided a nasal portion of the conjunctival cover on a nasal portion of the conjunctiva and a divided temporal portion of the conjunctival cover on a temporal portion of the conjunctiva, wherein the nasal portion and the temporal portion are separated from each other by at least one arcuate opening located at least one of superiorly and inferiorly; and
releasing the eye lids.

13. The method of claim 12, further comprising incorporating a drug into the annular conjunctival cover prior to application.

14. The method of claim 13, further comprising incorporating the drug into the annular conjunctival cover by exposing the annular conjunctival cover to the drug in solution or suspension such that the drug is absorbed into the annular conjunctival cover.

15. The method of claim 13, further comprising incorporating the drug into the annular conjunctival cover by inserting the drug into a drug reservoir incorporated in the annular conjunctival cover.

16. The method of claim 15, further comprising inserting multiple drugs into multiple separate drug reservoirs incorporated in the annular conjunctival cover.

* * * * *